United States Patent
Dawson et al.

(10) Patent No.: US 11,065,136 B2
(45) Date of Patent: Jul. 20, 2021

(54) VASCULAR EXPANDABLE DEVICES

(71) Applicant: Covidien LP, Mansfield, MA (US)

(72) Inventors: Marc Dawson, Mission Viejo, CA (US); Agee Barooni, Irvine, CA (US); Gregory M Hamel, Oakland, CA (US); Anthony Huynh, Wildomar, CA (US); Brad Jackson, San Diego, CA (US)

(73) Assignee: COVIDIEN LP, Mansfield, MA (US)

( * ) Notice: Subject to any disclaimer, the term of this patent is extended or adjusted under 35 U.S.C. 154(b) by 158 days.

(21) Appl. No.: 15/892,293

(22) Filed: Feb. 8, 2018

(65) Prior Publication Data

US 2019/0240050 A1 Aug. 8, 2019

(51) Int. Cl.
*A61F 2/90* (2013.01)
*A61F 2/91* (2013.01)
*A61F 2/82* (2013.01)

(52) U.S. Cl.
CPC .................. *A61F 2/90* (2013.01); *A61F 2/91* (2013.01); *A61F 2002/823* (2013.01); *A61F 2240/001* (2013.01); *A61F 2250/0067* (2013.01); *A61F 2250/0098* (2013.01)

(58) Field of Classification Search
CPC ...... A61F 2/86; A61F 2/90; A61F 2/91; A61F 2/966; A61F 2002/823; A61F 2250/0023; A61F 2250/0067; A61F 2250/0098; A61F 2240/001; A61F 2002/825; A61C 8/0015; A61C 8/0013
See application file for complete search history.

(56) References Cited

U.S. PATENT DOCUMENTS

| | | |
|---|---|---|
| 2,919,467 A | 1/1960 | Mercer |
| 5,336,205 A | 8/1994 | Zenzen et al. |
| 5,354,295 A | 10/1994 | Guglielmi et al. |
| 5,546,880 A | 8/1996 | Ronyak et al. |
| 5,630,840 A * | 5/1997 | Mayer ...................... A61F 2/86 606/194 |

(Continued)

FOREIGN PATENT DOCUMENTS

| | | |
|---|---|---|
| CN | 102727332 A | 10/2012 |
| CN | 103735266 A | 4/2014 |

(Continued)

OTHER PUBLICATIONS

International Search Report and Written Opinion dated May 16, 2019; International Application No. PCT/US2019/014788; 13 pages.

(Continued)

*Primary Examiner* — Jocelin C Tanner
(74) *Attorney, Agent, or Firm* — Fortem IP LLP; Mary Fox

(57) ABSTRACT

Vascular expandable devices and associated methods are disclosed herein. An expandable vascular device can be implantable across an aneurysm in a blood vessel of a patient. The device can include a generally tubular structure formed of a plurality of braided metallic elements. The device can have a compressed state with a compressed state diameter of 0.027 inches or less and an expanded state with an expanded state diameter of 1.75 mm or more. Each of the plurality of metallic strands can have an oxide layer having a thickness of about 400 angstroms or less. The tubular structure can be configured to self-expand from the compressed state to the expanded state.

33 Claims, 4 Drawing Sheets

(56) References Cited

U.S. PATENT DOCUMENTS

| | | |
|---|---|---|
| 5,669,931 A | 9/1997 | Kupiecki et al. |
| 5,718,159 A | 2/1998 | Thompson |
| 5,741,325 A | 4/1998 | Chaikof et al. |
| 5,951,599 A | 9/1999 | McCrory |
| 5,984,957 A | 11/1999 | Laptewicz, Jr. et al. |
| 6,012,277 A | 1/2000 | Prins et al. |
| 6,183,508 B1 | 2/2001 | Stinson |
| 6,231,598 B1 | 5/2001 | Berry et al. |
| 6,309,367 B1 | 10/2001 | Boock |
| 6,389,946 B1 | 5/2002 | Frid |
| 6,533,811 B1 | 3/2003 | Ryan et al. |
| 6,551,352 B2 | 4/2003 | Clerc et al. |
| 6,602,261 B2 | 8/2003 | Greene et al. |
| 6,605,101 B1 | 8/2003 | Schaefer et al. |
| 6,622,604 B1 | 9/2003 | Chouinard et al. |
| 6,660,024 B1 | 12/2003 | Flaherty et al. |
| 6,689,120 B1 | 2/2004 | Gerdts |
| 6,878,384 B2 | 4/2005 | Cruise et al. |
| 7,229,461 B2 | 6/2007 | Chin et al. |
| 7,601,160 B2 | 10/2009 | Richter |
| RE42,625 E | 8/2011 | Guglielmi |
| 8,043,326 B2 | 10/2011 | Hancock et al. |
| 8,425,541 B2 | 4/2013 | Masters et al. |
| 8,470,013 B2 | 6/2013 | Duggal et al. |
| 8,715,317 B1 | 5/2014 | Janardhan et al. |
| 8,876,886 B2 | 11/2014 | Kaufmann et al. |
| 8,906,057 B2 | 12/2014 | Connor et al. |
| 9,211,202 B2 | 12/2015 | Strother et al. |
| 9,486,224 B2 | 11/2016 | Riina et al. |
| 9,833,309 B2 | 12/2017 | Levi et al. |
| 9,844,380 B2 | 12/2017 | Furey |
| 9,907,684 B2 | 3/2018 | Connor et al. |
| 9,962,146 B2 | 5/2018 | Hebert et al. |
| 10,028,745 B2 | 7/2018 | Morsi |
| 2001/0000797 A1 | 5/2001 | Mazzocchi |
| 2001/0001835 A1 | 5/2001 | Greene et al. |
| 2001/0044651 A1 | 11/2001 | Steinke et al. |
| 2003/0018294 A1 | 1/2003 | Cox |
| 2003/0023299 A1* | 1/2003 | Amplatz ............... A61F 2/856 623/1.13 |
| 2003/0028209 A1 | 2/2003 | Teoh et al. |
| 2003/0040772 A1 | 2/2003 | Hyodoh et al. |
| 2003/0100945 A1* | 5/2003 | Yodfat ............... A61F 2/07 623/1.53 |
| 2003/0125258 A1 | 7/2003 | Lanctot et al. |
| 2003/0135265 A1* | 7/2003 | Stinson ............... D04C 1/06 623/1.16 |
| 2004/0073300 A1 | 4/2004 | Chouinard et al. |
| 2004/0088037 A1 | 5/2004 | Nachreiner et al. |
| 2004/0162606 A1 | 8/2004 | Thompson |
| 2004/0193246 A1 | 9/2004 | Ferrera |
| 2004/0215332 A1 | 10/2004 | Frid |
| 2004/0220663 A1 | 11/2004 | Rivelli, Jr. |
| 2004/0254628 A1 | 12/2004 | Nazzaro et al. |
| 2005/0038503 A1 | 2/2005 | Greenhalgh et al. |
| 2005/0090888 A1 | 4/2005 | Hines et al. |
| 2005/0137680 A1 | 6/2005 | Ortiz et al. |
| 2005/0197690 A1 | 9/2005 | Molaei et al. |
| 2005/0267511 A1 | 12/2005 | Marks et al. |
| 2006/0155323 A1 | 7/2006 | Porter et al. |
| 2006/0184238 A1 | 8/2006 | Kaufmann et al. |
| 2006/0200234 A1 | 9/2006 | Hines |
| 2006/0206199 A1 | 9/2006 | Churchwell et al. |
| 2007/0060994 A1 | 3/2007 | Gobran et al. |
| 2007/0100426 A1 | 5/2007 | Rudakov et al. |
| 2007/0175536 A1 | 8/2007 | Monetti et al. |
| 2007/0191924 A1 | 8/2007 | Rudakov |
| 2007/0293932 A1 | 12/2007 | Zilla et al. |
| 2008/0039930 A1 | 2/2008 | Jones et al. |
| 2008/0114391 A1 | 5/2008 | Dieck et al. |
| 2008/0221671 A1 | 9/2008 | Chouinard et al. |
| 2008/0234796 A1 | 9/2008 | Dorn |
| 2009/0177268 A1 | 7/2009 | Lundkvist et al. |
| 2009/0275974 A1 | 11/2009 | Marchand et al. |
| 2009/0326640 A1* | 12/2009 | Yoshimura ............... A61F 2/07 623/1.15 |
| 2010/0144895 A1 | 6/2010 | Porter |
| 2011/0137405 A1 | 6/2011 | Wilson et al. |
| 2011/0152998 A1 | 6/2011 | Berez et al. |
| 2012/0310319 A1* | 12/2012 | Tieu ............... A61F 2/852 623/1.4 |
| 2012/0316632 A1 | 12/2012 | Gao |
| 2013/0204351 A1* | 8/2013 | Cox ............... A61F 2/07 623/1.21 |
| 2013/0274866 A1 | 10/2013 | Cox et al. |
| 2014/0012307 A1 | 1/2014 | Franano et al. |
| 2014/0058420 A1 | 2/2014 | Hannes et al. |
| 2014/0172067 A1 | 6/2014 | Brown et al. |
| 2014/0228935 A1* | 8/2014 | Cattaneo ............... A61L 31/022 623/1.15 |
| 2014/0316012 A1 | 10/2014 | Freyman et al. |
| 2014/0371734 A1 | 12/2014 | Truckai |
| 2015/0148888 A1* | 5/2015 | Milner ............... A61F 2/88 623/1.22 |
| 2015/0216684 A1 | 8/2015 | Enzmann et al. |
| 2015/0250628 A1 | 9/2015 | Monstadt et al. |
| 2015/0313737 A1 | 11/2015 | Tippett et al. |
| 2015/0327843 A1 | 11/2015 | Garrison |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0206452 A1 | 7/2016 | Berez et al. |
| 2016/0256598 A1* | 9/2016 | Zucker ............... A61L 27/04 |
| 2017/0035588 A1 | 2/2017 | Sheldon et al. |
| 2017/0095358 A1* | 4/2017 | Savage ............... A61L 31/148 |
| 2017/0150971 A1 | 6/2017 | Hines |
| 2017/0156903 A1 | 6/2017 | Shobayashi |
| 2017/0189035 A1 | 7/2017 | Porter |
| 2017/0265869 A1* | 9/2017 | Cibulski ............... A61B 17/12118 |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2018/0207325 A1* | 7/2018 | Hasan ............... A61L 31/16 |
| 2019/0053811 A1 | 2/2019 | Garza et al. |
| 2019/0239895 A1 | 8/2019 | Dawson et al. |
| 2019/0240049 A1 | 8/2019 | Dawson et al. |
| 2019/0240050 A1 | 8/2019 | Dawson et al. |

FOREIGN PATENT DOCUMENTS

| | | |
|---|---|---|
| CN | 105592826 A | 5/2016 |
| CN | 205411404 U | 8/2016 |
| CN | 205434010 U | 8/2016 |
| CN | 106456422 A | 2/2017 |
| EP | 2586386 | 5/2013 |
| WO | WO1999/002092 | 4/1985 |
| WO | WO1995/009586 | 4/1995 |
| WO | WO1999/049812 | 10/1999 |
| WO | WO2001/005331 | 1/2001 |
| WO | WO2002/047579 | 6/2002 |
| WO | WO2003/043527 | 5/2003 |
| WO | WO2003/049600 | 6/2003 |
| WO | WO2005/115118 | 12/2005 |
| WO | 2006094941 A1 | 9/2006 |
| WO | 2011066962 A1 | 6/2011 |
| WO | 2012087301 A1 | 6/2012 |
| WO | 2017023527 A1 | 2/2017 |
| WO | 2017074411 A1 | 5/2017 |
| WO | 2018051187 A1 | 3/2018 |

OTHER PUBLICATIONS

U.S. Appl. No. 11/420,025, filed May 24, 2006.
U.S. Appl. No. 11/420,027, filed May 24, 2006.

(56) References Cited

OTHER PUBLICATIONS

U.S. Appl. No. 13/045,491, filed Mar. 10, 2011.
U.S. Appl. No. 13/775,592, filed Feb. 25, 2013.
U.S. Appl. No. 13/845,162, filed Mar. 18, 2013.
U.S. Appl. No. 14/791,876, filed Jul. 6, 2015.
U.S. Appl. No. 15/847,384, filed Dec. 19, 2017.
EP Opposition Brief filed Jun. 14, 2017 in EP Patent No. 2626038 (formerly EP App. No. 13164545.9).
NPL filed in support of EP Opposition Brief filed Jun. 14, 2017 in EP Patent No. 2626038 (formerly EP App. No. 13164545.9).
Maldonado, et al., "Stent Assisted Techniques for Intracranial Aneurysms," InTechOpen, Published Aug. 29, 2012, Chapter 14.
Gyula Gal, "New Devices for Exclusion of Cerebral Aneurysms," Urgent Interventional Therapies, First Edition, 2015; Chapter 35.
Nov. 30, 2017 Response to the EP Opposition Brief filed Jun. 14, 2017 in EP Patent No. 2626038 (formerly EP App. No. 13164545.9).
Search Report dated Mar. 25, 2020, CN Application No. 201910094390.6, 13 pages.
Search Report dated Mar. 25, 2020, CN Application No. 201910094404.4, 13 pages.
Search Report dated Mar. 20, 2020, CN Application No. 201910094405.9, 14 pages.

\* cited by examiner

VASCULAR EXPANDABLE DEVICES

TECHNICAL FIELD

The present technology relates generally to implantable devices for diverting blood flow in a blood vessel, and particularly to inhibiting blood flow into an aneurysm.

BACKGROUND

Aneurysms are an abnormal bulging or ballooning of a blood vessel that can result from the vessel wall being weakened by disease, injury, or a congenital abnormality. Aneurysms have thin, weak walls and a tendency to rupture, which can lead to stroke, death, disability, etc. One method of treating aneurysms includes inserting a flow-diverting stent or braid into a parent vessel that includes the aneurysm to be treated. Such stents or braids can be inserted into a vessel in a collapsed state, positioned next to the neck of the aneurysm, and expanded into apposition with the vessel wall. If the stent or braid has a sufficiently low porosity, it can function to block the flow of blood through the device and into the aneurysm to induce embolization of the aneurysm.

However, some aneurysms—and especially cerebral aneurysms—are located in small and tortuous portions of the vasculature. Current designs for flow-diverting stents or braids have difficulty approximating the vessel wall across the neck of the aneurysm if the parent vessel is curved, twisted, or forked. For example, current designs generally suffer from crimping or kinking when positioned in such tortuous vessels. This can make it more difficult to position a flow-diverting device and can cause the device to have an inadequate porosity as the device is expanded within the vessel. Also, current designs often undesirably block blood flow to branching or secondary vessels that are close to the aneurysm. Accordingly, there exists a need for improved flow-diverting devices for treating aneurysms.

SUMMARY

The present technology is directed to expandable devices configured to be positioned in a blood vessel lumen across the neck of an aneurysm to inhibit the flow of blood through the expandable device into the aneurysm to a degree sufficient to lead to thrombosis and healing of the aneurysm. The expandable devices of the present technology may be formed of a plurality of braided or woven strands, at least some of which have individual diameters less than 0.001 inches (25.4 µm). The expandable devices disclosed herein have improved flexibility, shape retention, and opening force over a range of expanded diameters. Some aspects of the present technology include expandable devices that have been heat set according to, for example, a novel heat setting process disclosed herein. The resulting expandable devices have a reduced oxide layer thickness and improved shape retention over a range of strand sizes.

The subject technology is illustrated, for example, according to various aspects described below, including with reference to FIGS. 1A-5B. Various examples of aspects of the subject technology are described as numbered clauses (1, 2, 3, etc.) for convenience. These are provided as examples and do not limit the subject technology.

Clause 1. An expandable device implantable across an aneurysm in a blood vessel of a patient, the expandable device comprising:

a generally tubular structure formed of a plurality of braided strands, the tubular structure having a proximal end, a distal end, and a length between the proximal end and the distal end;

each of the plurality of strands having a diameter that is 0.002 inches (0.0508 mm) or less, and each of at least some of the plurality of strands having a diameter that is 0.0009 inches (0.02286 mm) or less; and the expandable device having a compressed state and an expanded state, and being self-expandable from the compressed state to the expanded state, in which the expandable device has an expanded state diameter of at least 1.75 mm.

Clause 2. The expandable device of Clause 1, wherein the expandable device is compressible from the expanded state to the compressed state in which the expandable device has a diameter of 0.027 inches (0.6858 mm) or less.

Clause 3. The expandable device of Clause 1, wherein the expandable device is compressible from the expanded state to the compressed state in which the expandable device has a diameter of 0.021 inches (0.5334 mm) or less.

Clause 4. The expandable device of Clause 1, wherein the expandable device is compressible from the expanded state to the compressed state in which the expandable device has a diameter of 0.017 inches (0.4318 mm) or less.

Clause 5. The expandable device of any one of Clauses 1-4, wherein each of at least some of the plurality of strands comprise a core material surrounded by an outer material.

Clause 6. The expandable device of Clause 5, wherein the core material is a radiopaque material and the outer material is a resilient material.

Clause 7. The expandable device of any one of Clauses 1-6, wherein the plurality of strands comprises 48 strands.

Clause 8. The expandable device of any one of Clauses 1-7, wherein the PPI of the expandable device in the expanded state is from about 250 PPI to about 275 PPI.

Clause 9. The expandable device of any one of Clauses 1-6 or 8, wherein the plurality of strands comprises 64 strands.

Clause 10. The expandable device of any one of Clauses 1-7 or 9, wherein the PPI of the expandable device in the expanded state is from about 150 PPI to about 200 PPI.

Clause 11. The expandable device of any one of Clauses 1-10, wherein the expanded state diameter is from about 2.5 mm to about 3.5 mm.

Clause 12. The expandable device of any one of Clauses 1-10, wherein the expanded state diameter is from about 4 mm to about 6 mm.

Clause 13. The expandable device of any one of Clauses 1-12, wherein the expandable device is sized for deployment next to a vascular aneurysm, and wherein a sidewall of the expandable device has a porosity configured to inhibit flow of blood through the sidewall into the aneurysm to a degree sufficient to lead to thrombosis and healing of the aneurysm.

Clause 14. The expandable device of any one of Clauses 1-13, wherein the expandable device is sized for deployment next to a vascular aneurysm, and wherein a sidewall of the expandable device has a pore size configured to inhibit flow of blood through the sidewall into the aneurysm to a degree sufficient to lead to thrombosis and healing of the aneurysm.

Clause 15. The expandable device of any one of Clauses 1-14, wherein the tubular structure defines an internal lumen and has openings at the proximal and distal ends of the tubular structure.

Clause 16. The expandable device of Clause 15, wherein the lumen is non-filtering and open to flow of liquid therethrough.

Clause 17. The expandable device of any one of Clauses 1-16, wherein the tubular structure consists of the braided strands.

Clause 18. A method comprising:
positioning an expandable device in a blood vessel across an aneurysm in a compressed state within a delivery catheter, wherein the expandable device is a generally tubular structure formed of a plurality of braided strands, and wherein each of the plurality of strands have a diameter that is 0.002 inches (0.0508 mm) or less, and each of at least some of the plurality of strands have a diameter that is 0.0009 inches (0.02286 mm) or less; and
expanding the expandable device by withdrawing the delivery catheter proximally and releasing the expandable device from the compressed state, wherein the expandable device expands to an expanded state diameter of at least 1.75 mm,
wherein, in the expanded state, the expandable device inhibits the flow of blood through a sidewall of the expandable device into the aneurysm to a degree sufficient to lead to thrombosis and healing of the aneurysm.

Clause 19. The method of Clause 18, wherein the delivery catheter has an inner diameter of 0.027 inches or less.

Clause 20. The method of Clause 18 or Clause 19, wherein each of at least some of the plurality of strands comprise a core material surrounded by an outer material.

Clause 21. The method of Clause 20, wherein the core material is a radiopaque material and the outer material is a resilient material.

Clause 22. The method of any one of Clauses 18-21, wherein the expandable device expands to an expanded state diameter from about 2.5 mm to about 3.5 mm, and wherein the plurality of strands comprises 48 strands.

Clause 23. The method of any one of Clauses 18-21, wherein the expandable device expands to an expanded state diameter from about 4 mm to about 6 mm, and wherein the plurality of strands comprises 64 strands.

Clause 24. A system comprising:
a core assembly; and
a generally tubular structure disposed on the core assembly, wherein:
the tubular structure is formed of a plurality of braided strands, and has a proximal end, a distal end, and a length between the proximal end and the distal end;
each of the plurality of strands has a diameter that is 0.002 inches (0.0508 mm) or less, and each of at least some of the plurality of strands has a diameter that is 0.0009 inches (0.02286 mm) or less; and
the tubular structure has a compressed state and an expanded state, and is self-expandable from the compressed state to the expanded state, in which the tubular structure has an expanded state diameter of at least 1.75 mm.

Clause 25. The system of Clause 24, further comprising a tubular sheath, and the core assembly and tubular structure are disposed in a lumen of the tubular sheath.

Clause 26. The system of Clause 1, wherein the tubular structure is compressible from the expanded state to the compressed state in which the tubular structure has a diameter of 0.027 inches (0.6858 mm) or less.

Clause 27. The system of Clause 1, wherein the tubular structure is compressible from the expanded state to the compressed state in which the tubular structure has a diameter of 0.021 inches (0.5334 mm) or less.

Clause 28. The system of Clause 24, wherein the tubular structure is compressible from the expanded state to the compressed state in which the tubular structure has a diameter of 0.017 inches (0.4318 mm) or less.

Clause 29. The system of any one of Clauses 24-28, wherein each of at least some of the plurality of strands comprise a core material surrounded by an outer material.

Clause 30. The system of Clause 29, wherein the core material is a radiopaque material and the outer material is a resilient material.

Clause 31. The system of any one of Clauses 24-30, wherein the plurality of strands comprises 48 strands.

Clause 32. The system of any one of Clauses 24-31, wherein the PPI of the tubular structure in the expanded state is from about 250 PPI to about 275 PPI.

Clause 33. The system of any one of Clauses 24-30 or 32, wherein the plurality of strands comprises 64 strands.

Clause 34. The system of any one of Clauses 24-31 or 33, wherein the PPI of the tubular structure in the expanded state is from about 150 PPI to about 200 PPI.

Clause 35. The system of any one of Clauses 24-34, wherein the expanded state diameter is from about 2.5 mm to about 3.5 mm.

Clause 36. The system of any one of Clauses 24-34, wherein the expanded state diameter is from about 4 mm to about 6 mm.

Clause 37. The system of any one of Clauses 24-36, wherein the tubular structure is sized for deployment next to a vascular aneurysm, and wherein a sidewall of the tubular structure has a porosity configured to inhibit flow of blood through the sidewall into the aneurysm to a degree sufficient to lead to thrombosis and healing of the aneurysm.

Clause 38. The system of any one of Clauses 24-37, wherein the tubular structure is sized for deployment next to a vascular aneurysm, and wherein a sidewall of the tubular structure has a pore size configured to inhibit flow of blood through the sidewall into the aneurysm to a degree sufficient to lead to thrombosis and healing of the aneurysm.

Clause 39. The system of any one of Clauses 24-38, wherein the tubular structure defines an internal lumen and has openings at the proximal and distal ends of the tubular structure.

Clause 40. The system of Clause 39, wherein the lumen is non-filtering and open to flow of liquid therethrough.

Clause 41. The system of any one of Clauses 24-40, wherein the tubular structure consists of the braided strands.

Clause 42. An expandable device implantable across an aneurysm in a blood vessel of a patient, the expandable device comprising:
a generally tubular sidewall formed of a plurality of braided strands;
a compressed state for delivery through a delivery catheter, the expandable device having a compressed state diameter of 0.027 inches or less, corresponding to an inside diameter of the delivery catheter;
an expanded state in which the expandable device attains an expanded state diameter corresponding to the expandable device; and
a full expansion distance corresponding to the longitudinal distance beyond a distal opening of the delivery catheter at which the distal end of the expandable device attains the expanded state diameter,
wherein the full expansion distance is 20 mm or less.

Clause 43. The expandable device of Clause 42, wherein the full expansion distance is 5-14 mm.

Clause 44. The expandable device of Clause 42 or Clause 43, wherein the expanded state diameter is 2 mm or more.

Clause 45. The expandable device of any one of Clauses 42-44, wherein the expanded state diameter is 2-6 mm.

Clause 46. The expandable device of any one of Clauses 42-45, wherein the compressed state diameter is 0.021 inches or less.

Clause 47. The expandable device of any one of Clauses 42-45, wherein the compressed state diameter is 0.017 inches or less.

Clause 48. The expandable device of any one of Clauses 42-45, wherein the compressed state diameter is 0.017-0.027 inches.

Clause 49. The expandable device of any one of Clauses 42-48, wherein the expanded state diameter is 2 mm or more.

Clause 50. The expandable device of any one of Clauses 42-49, wherein the expanded state diameter is 2-6 mm.

Clause 51. The expandable device of any one of Clauses 42-50, wherein the sidewall has a number of pores between the strands, and the pores are sized to have a flow-diversion effect with respect to an aneurysm when the sidewall extends across the aneurysm.

Clause 52. The expandable device of any one of Clauses 42-51, wherein the sidewall has a number of pores between the strands, and a porosity measure that is sufficient to have a flow-diversion effect with respect to an aneurysm when the sidewall extends across the aneurysm.

Clause 53. The expandable device of any one of Clauses 42-52, wherein the strands have a cross-sectional diameter of 0.002 inches or less.

Clause 54. The expandable device of any one of Clauses 42-53, wherein the strands have a cross-sectional diameter of 0.0015 inches or less.

Clause 55. The expandable device of any one of Clauses 42-54, wherein at least some of the strands have a cross-sectional diameter of 0.0009 inches or less.

Clause 56. The expandable device of any one of Clauses 42-55, wherein at least some of the strands are metallic and have an oxide layer that is 400 angstroms or less in thickness.

Clause 57. The expandable device of any one of Clauses 42-56, wherein the expandable device is self-expandable to the expanded state diameter.

Clause 58. The expandable device of any one of Clauses 42-57, wherein the sidewall forms a tube with a lumen defined by the sidewall, and openings at the proximal and distal ends of the tube.

Clause 59. The expandable device of Clause 58, wherein the lumen is non-filtering and open to flow of liquid therethrough.

Clause 60. The expandable device of any one of Clauses 42-59, wherein the sidewall consists of the braided strands.

Clause 61. The expandable device of any one of Clauses 42-60, wherein the strands collectively comprise a first metallic material and a second metallic material, and the second metallic material is more radiopaque than the first metallic material.

Clause 62. The expandable device of Clause 61, wherein the second metallic material comprises platinum or platinum alloy.

Clause 63. The expandable device of any one of Clauses 42-62, wherein the expanded state diameter is a diameter to which the expandable device will self-expand, and is 2.5%-12.5% below the expandable device's maximum unconstrained self-expansion diameter.

Clause 64. An expandable device implantable across an aneurysm in a blood vessel of a patient, the expandable device comprising:

a generally tubular sidewall formed of a plurality of braided strands;

a compressed state for delivery through a delivery catheter, the expandable device having a compressed state diameter of 0.027 inches or less, corresponding to an inside diameter of the delivery catheter; and a first expansion distance corresponding to the longitudinal distance beyond a distal opening of the catheter at which the distal end of the expandable device first expands beyond the compressed state diameter, wherein the first expansion distance is 12 mm or less.

Clause 65. The expandable device of Clause 64, wherein the first expansion distance is 3-7 mm.

Clause 66. The expandable device of Clause 64 or Clause 65, wherein the compressed state diameter is 0.021 inches or less.

Clause 67. The expandable device of Clause 64 or Clause 65, wherein the compressed state diameter is 0.017 inches or less.

Clause 68. The expandable device of Clause 64 or Clause 65, wherein the compressed state diameter is 0.017-0.027 inches.

Clause 69. The expandable device of any one of Clauses 64-68, wherein the sidewall has a number of pores between the strands, and the pores are sized to have a flow-diversion effect with respect to an aneurysm when the sidewall extends across the aneurysm.

Clause 70. The expandable device of any one of Clauses 64-69, wherein the sidewall has a number of pores between the strands, and a porosity measure that is sufficient to have a flow-diversion effect with respect to an aneurysm when the sidewall extends across the aneurysm.

Clause 71. The expandable device of any one of Clauses 64-70, wherein the strands have a cross-sectional diameter of 0.002 inches or less.

Clause 72. The expandable device of any one of Clauses 64-70, wherein the strands have a cross-sectional diameter of 0.0015 inches or less.

Clause 73. The expandable device of any one of Clauses 64-70, wherein at least some of the strands have a cross-sectional diameter of 0.0009 inches or less.

Clause 74. The expandable device of any one of Clauses 64-73, wherein at least some of the strands are metallic and have an oxide layer that is 400 angstroms or less in thickness.

Clause 75. The expandable device of any one of Clauses 64-74, wherein the expandable device has an expanded state diameter of 2 mm or more.

Clause 76. The expandable device of any one of Clauses 64-75, wherein the expandable device has an expanded state diameter of 2-6 mm.

Clause 77. The expandable device of Clause 75 or Clause 76, wherein the expanded state diameter is a diameter to which the expandable device will self-expand, and is 2.5%-12.5% below the expandable device's maximum unconstrained self-expansion diameter.

Clause 78. The expandable device of any one of Clauses 64-77, wherein the expandable device is self-expandable from the compressed state diameter.

Clause 79. The expandable device of any one of Clauses 75-77, wherein the expandable device in its expanded state comprises a tube with a lumen defined by the sidewall, and openings at the proximal and distal ends of the tube.

Clause 80. The expandable device of Clause 79, wherein the lumen is non-filtering and open to flow of liquid therethrough.

Clause 81. The expandable device of any one of Clauses 64-80, wherein the sidewall consists of the braided strands.

Clause 82. The expandable device of any one of Clauses 64-81, wherein the strands collectively comprise a first metallic material and a second metallic material, and the second metallic material is more radiopaque than the first metallic material.

Clause 84. An expandable device comprising:
a generally tubular sidewall formed of a plurality of braided strands;
a compressed state for delivery of the expandable device, in which the expandable device has a compressed state diameter of 0.027 inches or less;
an expanded state in which the expandable device has an expanded state diameter corresponding to the expandable device; and
a full expansion distance corresponding to a longitudinal unconstrained distance at which the distal end of the expandable device attains the expanded state diameter, wherein the full expansion distance is 20 mm or less.

Clause 85. The expandable device of Clause 84, wherein the full expansion distance is 5-14 mm.

Clause 86. The expandable device of Clause 84 or Clause 85, wherein the expanded state diameter is 2 mm or more.

Clause 87. The expandable device of Clause 84 or Clause 85, wherein the expanded state diameter is 2-6 mm.

Clause 88. The expandable device of any one of Clauses 84-87, wherein the compressed state diameter is 0.021 inches or less.

Clause 89. The expandable device of any one of Clauses 84-87, wherein the compressed state diameter is 0.017 inches or less.

Clause 90. The expandable device of any one of Clauses 84-87, wherein the compressed state diameter is 0.017-0.027 inches.

Clause 91. The expandable device of any one of Clauses 84-90, wherein the sidewall has a number of pores between the strands, and the pores are sized to have a flow-diversion effect with respect to an aneurysm when the sidewall extends across the aneurysm.

Clause 92. The expandable device of any one of Clauses 84-91, wherein the sidewall has a number of pores between the strands, and a porosity measure that is sufficient to have a flow-diversion effect with respect to an aneurysm when the sidewall extends across the aneurysm.

Clause 93. The expandable device of any one of Clauses 84-92, wherein the strands have a cross-sectional diameter of 0.002 inches or less.

Clause 94. The expandable device of any one of Clauses 84-92, wherein the strands have a cross-sectional diameter of 0.0015 inches or less.

Clause 95. The expandable device of any one of Clauses 84-92, wherein at least some of the strands have a cross-sectional diameter of 0.0009 inches or less.

Clause 96. The expandable device of any one of Clauses 84-95, wherein at least some of the strands are metallic and have an oxide layer that is 400 angstroms or less in thickness.

Clause 97. The expandable device of any one of Clauses 84-96, wherein the expandable device is self-expandable to the expanded state diameter.

Clause 98. The expandable device of any one of Clauses 84-97, wherein the sidewall forms a tube with a lumen defined by the sidewall, and openings at the proximal and distal ends of the tube.

Clause 99. The expandable device of Clause 98, wherein the lumen is non-filtering and open to flow of liquid therethrough.

Clause 100. The expandable device of any one of Clauses 84-99, wherein the sidewall consists of the braided strands.

Clause 101. The expandable device of any one of Clauses 84-100, wherein the strands collectively comprise a first metallic material and a second metallic material, and the second metallic material is more radiopaque than the first metallic material.

Clause 102. The expandable device of Clause 101, wherein the second metallic material comprises platinum or platinum alloy.

Clause 103. The expandable device of any one of Clauses 84-102, wherein the expanded state diameter is a diameter to which the expandable device will self-expand, and is 2.5%-12.5% below the expandable device's maximum unconstrained self-expansion diameter.

Clause 104. An expandable device comprising:
a generally tubular sidewall formed of a plurality of braided strands;
a compressed state for delivery of the expandable device, in which the expandable device has a compressed state diameter of 0.027 inches or less; and
a first expansion distance corresponding to a longitudinal unconstrained distance at which the distal end of the expandable device first expands beyond the compressed state diameter, and
wherein the first expansion distance is 12 mm or less.

Clause 105. The expandable device of Clause 104, wherein the first expansion distance is 3-7 mm.

Clause 106. The expandable device of Clause 104 or Clause 105, wherein the compressed state diameter is 0.021 inches or less.

Clause 107. The expandable device of Clause 104 or Clause 105, wherein the compressed state diameter is 0.017 inches or less.

Clause 108. The expandable device of Clause 104 or Clause 105, wherein the compressed state diameter is 0.017-0.027 inches.

Clause 109. The expandable device of any one of Clauses 104-108, wherein the sidewall has a number of pores between the strands, and the pores are sized to have a flow-diversion effect with respect to an aneurysm when the sidewall extends across the aneurysm.

Clause 110. The expandable device of any one of Clauses 104-109, wherein the sidewall has a number of pores between the strands, and a porosity measure that is sufficient to have a flow-diversion effect with respect to an aneurysm when the sidewall extends across the aneurysm.

Clause 111. The expandable device of any one of Clauses 104-110, wherein the strands have a cross-sectional diameter of 0.002 inches or less.

Clause 112. The expandable device of any one of Clauses 104-110, wherein the strands have a cross-sectional diameter of 0.0015 inches or less.

Clause 113. The expandable device of any one of Clauses 104-112, wherein at least some of the strands have a cross-sectional diameter of 0.0009 inches or less.

Clause 114. The expandable device of any one of Clauses 104-113, wherein at least some of the strands are metallic and have an oxide layer that is 400 angstroms or less in thickness.

Clause 115. The expandable device of any one of Clauses 104-114, wherein the expandable device has an expanded state diameter of 2 mm or more.

Clause 116. The expandable device of any one of Clauses 104-114, wherein the expandable device has an expanded state diameter of 2-6 mm.

Clause 117. The expandable device of Clause 115 or Clause 116, wherein the expanded state diameter is a diameter to which the expandable device will self-expand, and is 2.5%-12.5% below the expandable device's maximum unconstrained self-expansion diameter.

Clause 118. The expandable device of any one of Clauses 104-117, wherein the expandable device is self-expandable from the compressed state diameter.

Clause 119. The expandable device of any one of Clauses 104-118, wherein the expandable device in its expanded state comprises a tube with a lumen defined by the sidewall, and openings at the proximal and distal ends of the tube.

Clause 120. The expandable device of Clause 119, wherein the lumen is non-filtering and open to flow of liquid therethrough.

Clause 121. The expandable device of any one of Clauses 104-120, wherein the sidewall consists of the braided strands.

Clause 122. The expandable device of any one of Clauses 104-121, wherein the strands collectively comprise a first metallic material and a second metallic material, and the second metallic material is more radiopaque than the first metallic material.

Clause 123. The expandable device of Clause 122, wherein the second metallic material comprises platinum or a platinum alloy.

Clause 124. An expandable device comprising:
a generally tubular sidewall formed of a plurality of braided strands;
a compressed state for delivery of the expandable device, in which the expandable device has a compressed state diameter of 0.027 inches or less;
an expanded state in which the expandable device has an expanded state diameter corresponding to the expandable device;
a first expansion distance corresponding to a first longitudinal unconstrained distance at which the distal end of the expandable device first expands beyond the compressed state diameter, the first expansion distance being 12 mm or less; and
a full expansion distance corresponding to a second longitudinal unconstrained distance at which the distal end of the expandable device attains the expanded state diameter, the full expansion distance being 20 mm or less.

Clause 125. A system comprising:
a core assembly; and
a generally tubular structure disposed on the core assembly, wherein the tubular structure is formed of a plurality of braided strands, and wherein the tubular structure has:
a compressed state for delivery of the expandable device,
an expanded state in which the tubular structure has an expanded state diameter corresponding to the tubular structure, and
a full expansion distance corresponding to a longitudinal unconstrained distance at which the distal end of the expandable device attains the expanded state diameter, wherein the full expansion distance is 20 mm or less.

Clause 126. The system of Clause 125, further comprising a tubular sheath, and the core assembly and tubular structure are disposed in a lumen of the tubular sheath.

Clause 127. The system of Clause 126, wherein the tubular sheath is a first tubular sheath, and wherein the system further comprises a second tubular sheath.

Clause 128. The system of any one of Clauses 125-127, wherein the tubular structure has a compressed state diameter of 0.027 inches or less.

Clause 129. The system of any one of Clauses 125-128, wherein the full expansion distance is 5-14 mm.

Clause 130. A system comprising:
a core assembly; and
a generally tubular structure disposed on the core assembly, wherein the tubular structure is formed of a plurality of braided strands, and wherein the tubular structure has:
a compressed state for delivery of the expandable device,
a first expansion distance corresponding to a longitudinal unconstrained distance at which the distal end of the expandable device first expands beyond the compressed state diameter, wherein the first expansion distance is 12 mm or less.

Clause 131. The system of Clause 130, further comprising a tubular sheath, and the core assembly and tubular structure are disposed in a lumen of the tubular sheath.

Clause 132. The system of Clause 131, wherein the tubular sheath is a first tubular sheath, and wherein the system further comprises a second tubular sheath.

Clause 133. The system of any one of Clauses 130-132, wherein the tubular structure has a compressed state diameter of 0.027 inches or less.

Clause 134. The system of any one of Clauses 130-133, wherein the first expansion distance is 3-7 mm.

Clause 135. A method comprising:
positioning a delivery catheter containing an expandable device in a compressed state in a blood vessel, the expandable device comprising a generally tubular structure formed of a plurality of braided strands, wherein the expandable device has an expanded state in which the expandable device attains an expanded state diameter corresponding to the expandable device; and
expanding a distal end of the expandable device to the expanded state diameter when the distal end is a longitudinal distance of 20 mm or less beyond a distal opening of the delivery catheter.

Clause 136. The method of Clause 135, wherein expanding the distal end of the expandable device includes withdrawing the delivery catheter proximally beyond the distal end.

Clause 137. The method of Clause 135 or Clause 136, further comprising expanding the entire length of the expandable device to the expanded state diameter.

Clause 138. The method of any one of Clauses 135-137, further comprising positioning the expandable device in the expanded state across a neck of an aneurysm in the blood vessel.

Clause 139. The method of Clause 138, wherein, in the expanded state, the expandable device inhibits the flow of blood through a sidewall of the expandable device into the aneurysm to a degree sufficient to lead to thrombosis and healing of the aneurysm.

Clause 140. The method of any one of Clauses 135-139, wherein the longitudinal distance is 5-14 mm.

Clause 141. The method of any one of Clauses 135-140, wherein the expandable device is self-expandable to the expanded state diameter.

Clause 142. The method of any one of Clauses 135-137, wherein the expandable device has a diameter in the compressed state of 0.027 inches or less.

Clause 143. The method of any one of Clauses 135-142, wherein the expandable device is any of the expandable devices of Clauses 1-17 and 42-124.

Clause 144. A method comprising:
positioning a delivery catheter containing an expandable device in a compressed state in a blood vessel, the expandable device comprising a generally tubular structure formed of a plurality of braided strands; and
expanding a distal end of the expandable device beyond its diameter in the compressed state when the distal end is a longitudinal distance of 12 mm or less beyond a distal opening of the delivery catheter.

Clause 145. The method of Clause 144, wherein the expandable device has a diameter in the compressed state of 0.027 inches or less.

Clause 146. The method of Clause 144 or Clause 145, wherein expanding the distal end of the expandable device includes withdrawing the delivery catheter proximally beyond the distal end.

Clause 147. The method of any one of Clauses 144-146, wherein the expandable device has an expanded state in which the expandable device attains an expanded state diameter corresponding to the expandable device, and wherein the method further comprises expanding the entire length of the expandable device to the expanded state diameter.

Clause 148. The method of any one of Clauses 144-147, further comprising positioning the expandable device in an expanded state across a neck of an aneurysm in the blood vessel.

Clause 149. The method of Clause 148, wherein, in the expanded state, the expandable device inhibits the flow of blood through a sidewall of the expandable device into the aneurysm to a degree sufficient to lead to thrombosis and healing of the aneurysm.

Clause 150. The method of any one of Clauses 144-149, wherein the longitudinal distance is 3-7 mm.

Clause 151. The method of any one of Clauses 144-150, wherein the expandable device is self-expandable.

Clause 152. The method of any one of Clauses 144-151, wherein the expandable device is any of the expandable devices of Clauses 1-17 and 42-124.

Clause 153. An expandable device implantable across an aneurysm in a blood vessel of a patient, the expandable device comprising:
a generally tubular structure formed of a plurality of braided metallic strands, the tubular structure having a proximal end, a distal end, and a length between the proximal end and the distal end;
a compressed state in which the expandable device has a compressed state diameter of 0.027 inches or less;
an expanded state in which the expandable device has an expanded state diameter corresponding to the expandable device, the expanded state diameter being 1.75 mm or more;
wherein each of the plurality of metallic strands has an oxide layer having a thickness of about 400 angstroms or less, and
wherein the tubular structure is configured to self-expand from the compressed state to the expanded state.

Clause 154. The expandable device of Clause 153, wherein the oxide layer thickness is between 10 angstroms and 400 angstroms.

Clause 155. The expandable device of Clause 153, wherein the oxide layer thickness is between 100 angstroms and 350 angstroms.

Clause 156. The expandable device of Clause 153, wherein the oxide layer thickness is between 200 angstroms and 350 angstroms.

Clause 157. The expandable device of Clause 153, wherein the oxide layer thickness is between 200 angstroms and 300 angstroms.

Clause 158. The expandable device of any one of Clauses 153-157 wherein each of the plurality of strands has a diameter that is less than or equal to 0.002 inches (0.0508 mm).

Clause 159. The expandable device of any one of Clauses 153-157 wherein each of the plurality of strands has a diameter that is less than or equal to 0.0015 inches (0.0381 mm).

Clause 160. The expandable device of any one of Clauses 153-157 wherein each of the plurality of strands has a diameter that is less than or equal to 0.002 inches (0.0508 mm), and at least some of the plurality of strands have individual diameters less than or equal to 0.0009 inches (0.02286 mm).

Clause 161. The expandable device of any one of Clauses 153-160, wherein the compressed state diameter is 0.021 inches (0.5334 mm) or less.

Clause 162. The expandable device of any one of Clauses 153-160, wherein the compressed state diameter is 0.017 inches (0.4318 mm) or less.

Clause 163. The expandable device of any one of Clauses 153-160, wherein the compressed state diameter is 0.017-0.027 inches.

Clause 164. The expandable device of any one of Clauses 153-163, wherein the expanded state diameter is 2 mm or more.

Clause 165. The expandable device of any one of Clauses 153-163, wherein the expanded state diameter is 2-10 mm.

Clause 166. The expandable device of any one of Clauses 153-163, wherein the expanded state diameter is 2-6 mm.

Clause 167. The expandable device of any one of Clauses 153-166, wherein the braided strands form a sidewall of the tubular structure with a number of pores between the strands, and the pores are sized to have a flow-diversion effect with respect to an aneurysm when the sidewall extends across the aneurysm.

Clause 168. The expandable device of any one of Clauses 153-167, wherein the braided strands form a sidewall of the tubular structure with a number of pores between the strands, and the sidewall has a porosity measure that is sufficient to have a flow-diversion effect with respect to an aneurysm when the sidewall extends across the aneurysm.

Clause 169. The expandable device of any one of Clauses 153-168, wherein the tubular structure defines a lumen, and has openings at the proximal and distal ends of the structure.

Clause 170. The expandable device of Clause 169, wherein the lumen is non-filtering and open to flow of liquid therethrough.

Clause 171. The expandable device of any one of Clauses 153-170, wherein the tubular structure consists of the braided strands.

Clause 172. The expandable device of any one of Clauses 153-171, wherein the braided strands alone are sufficient to cause the tubular structure to self-expand to the expanded state.

Clause 173. The expandable device of any one of Clauses 153-172, wherein the strands collectively comprise a first metallic material and a second metallic material, and the second metallic material is more radiopaque than the first metallic material.

Clause 174. The expandable device of Clause 173, wherein the second metallic material comprises platinum or platinum alloy.

Clause 175. The expandable device of any one of Clauses 153-174, wherein the expanded state diameter is a diameter to which the expandable device will self-expand, and is 2.5%-12.5% below the expandable device's maximum unconstrained self-expansion diameter.

Clause 176. The expandable device of any one of Clauses 153-175, wherein the tubular structure is heat set to self-expand toward the expanded state diameter.

Clause 177. The expandable device of any one of Clauses 153-176, wherein the strands possess an anti-thrombogenic outer surface.

Clause 178. A method, comprising:
 positioning a plurality of metal strands on a mandrel; and
 heating the plurality of strands to a temperature greater than 600° F. and maintaining the temperature for a time of at least five minutes,
 wherein, after heating the plurality of strands for the time of at least five minutes, an outer surface of each of the filaments has an oxide layer no more than 400 angstroms thick.

Clause 179. The method of Clause 178 wherein the time for heating the plurality of strands is at least ten minutes.

Clause 180. The method of Clause 178 wherein the time for heating the plurality of strands is at least fifteen minutes.

Clause 181. The method of any one of Clauses 178-180 wherein the temperature is at least 625° C.

Clause 182. The method of any one of Clauses 178-180 wherein the temperature is at least 650° C.

Clause 183. The method of any one of Clauses 178-180 wherein the temperature is at least 675° C.

Clause 184. The method of any one of Clauses 178-180 wherein the temperature is at least 700° C.

Clause 185. The method of any one of Clauses 178-184 wherein the oxide layer is between 10 angstroms and 400 angstroms thick.

Clause 186. The method of any one of Clauses 178-184 wherein the oxide layer is between 200 angstroms and 350 angstroms thick.

Clause 187. The method of any one of Clauses 178-186 wherein each of the plurality of strands has a diameter that is less than or equal to 0.002 inches (0.0508 mm), and at least some of the plurality of strands have individual diameters less than or equal to 0.0009 inches (0.02286 mm).

Clause 188. The method of any one of Clauses 178-187 wherein at least some of the strands comprise a radiopaque core material surrounded by a resilient outer material.

Clause 189. The method of any one of Clauses 178-188 wherein heating the strands takes place in an oxygen-free chamber.

Clause 190. The method of any one of Clauses 178-189 wherein heating the strands takes place in a chamber containing hydrogen gas.

Clause 191. The method of any one of Clauses 178-190 wherein heating the strands takes place in a chamber containing a gas that has a chemically reducing effect on the metal of the strands.

Clause 192. The method of any one of Clauses 178-191 further comprising maintaining gas pressure in the chamber above 5 PSI during heating.

Clause 193. An expandable device implantable across an aneurysm in a blood vessel of a patient, the expandable device comprising:
 a generally tubular structure formed of a plurality of braided metallic strands, wherein each of the plurality of strands has a diameter that is less than or equal to 0.002 inches (0.0508 mm); and
 an expanded state in which the expandable device has an expanded state diameter corresponding to the expandable device, the expanded state diameter being 1.75 mm or more;
 wherein each of the plurality of metallic strands has an oxide layer having a thickness of about 400 angstroms or less, and
 wherein the tubular structure is configured to self-expand from the compressed state to the expanded state.

Clause 194. The expandable device of Clause 193, wherein the oxide layer thickness is between 10 angstroms and 400 angstroms.

Clause 195. The expandable device of Clause 193, wherein the oxide layer thickness is between 100 angstroms and 350 angstroms.

Clause 196. The expandable device of Clause 193, wherein the oxide layer thickness is between 200 angstroms and 350 angstroms.

Clause 197. The expandable device of Clause 193, wherein the oxide layer thickness is between 200 angstroms and 300 angstroms.

Clause 198. The expandable device of any one of Clauses 193-197, wherein the braided strands alone are sufficient to cause the tubular structure to self-expand to the expanded state.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
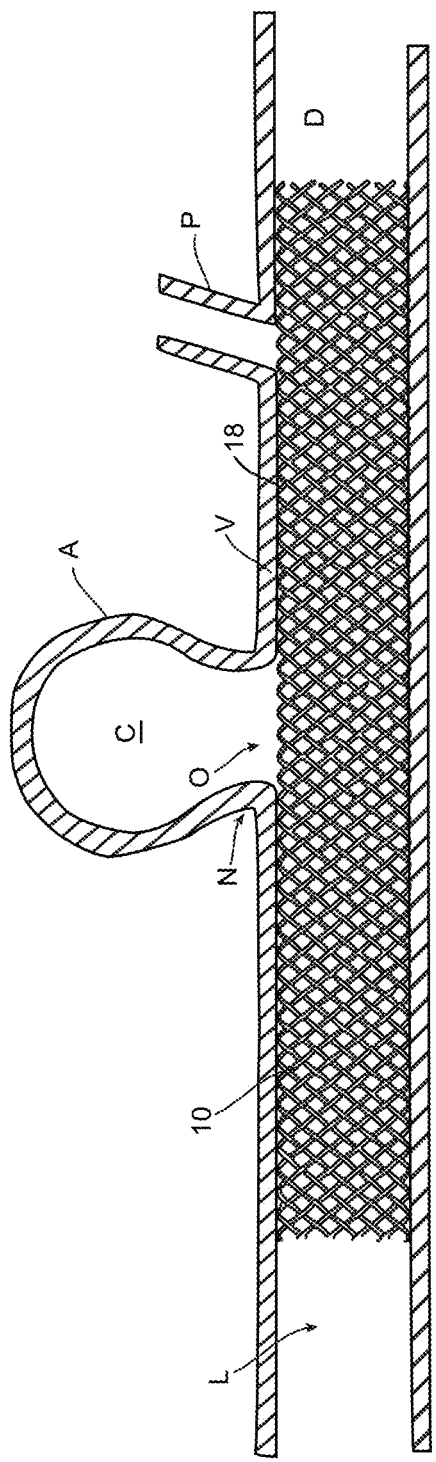
FIG. 1A is a side view of an expandable device in accordance with the present technology, shown in an expanded state positioned within a blood vessel across the neck of an aneurysm.

FIG. 1A is a side view of an expandable device 10 in accordance with the present technology, shown in an expanded state positioned within a blood vessel V (such as a cerebral blood vessel or cerebral artery, or a peripheral, coronary, pulmonary, abdominal, thoracic or aortic artery) across the neck N of an aneurysm A. As shown in FIG. 1A, the expandable device 10 may comprise a plurality of strands 18 that are braided or woven to form a generally tubular device 10 with a tubular sidewall as can be observed when the expandable device 10 is in the expanded state.

As used herein, the "expanded state diameter" is the diameter to which the expandable device 10 will self-expand, while remaining just short of full expansion (at which the expandable device 10 reaches its maximum or unconstrained diameter). Therefore, in the expanded state diameter, the expandable device 10 retains some capability to self-expand further. This enables the expandable device 10 to remain apposed to and in contact with the inner wall of the volume (e.g. a blood vessel or other body lumen, or a tube) in which the expandable device is deployed. The expanded state diameter will therefore typically correspond to the maximum vessel diameter or other body lumen diameter in which the expandable device 10 can be usefully deployed (sometimes referred to as the expandable device's "labeled diameter"). For example, the expanded state diameter of a given device 10 can be a slight amount, e.g. about 0.25 mm or about 2.5%-12.5%, less than the maximum diameter of the expandable device. In contrast to the expanded state diameter, the maximum diameter or unconstrained diameter of the expandable device 10 is the diameter to which the expandable device will self-expand, free of external constraint and without any assistance in expansion. The expanded state diameter and the maximum/unconstrained diameter are measured as outer diameters of the expandable device 10.

For example, in the expanded state, the expandable device 10 may have an expanded state diameter of 1.75 mm to about 7 mm, 2 mm to about 3.75 mm, 4 mm to about 6.25 mm, 2 mm to about 6.75 mm, 2.25 mm to about 6.50 mm, 2.5 mm to about 6.25 mm, 2.75 to about 6 mm, 3 mm to about 5.75 mm, 3.25 mm to about 5.50 mm, 3.5 mm to about 5.25 mm, 3.75 mm to about 5 mm, 4 mm to about 4.75 mm. In some embodiments, in the expanded state, the expandable device 10 may have an expanded state diameter of about 1.75 mm, about 2.00 mm, about 2.25 mm, about 2.50 mm, about 2.75 mm, about 3.00 mm, about 3.25 mm, about 3.50 mm, about 3.75 mm, about 4.00 mm, about 4.25 mm, about 4.50 mm, about 4.75 mm, about 5.00 mm, about 5.25 mm, about 5.50 mm, about 5.75 mm, about 6.00 mm, about 6.25 mm, about 6.50 mm, about 6.75 mm, about 7.00 mm, and other suitable diameters.

Figure 1B:
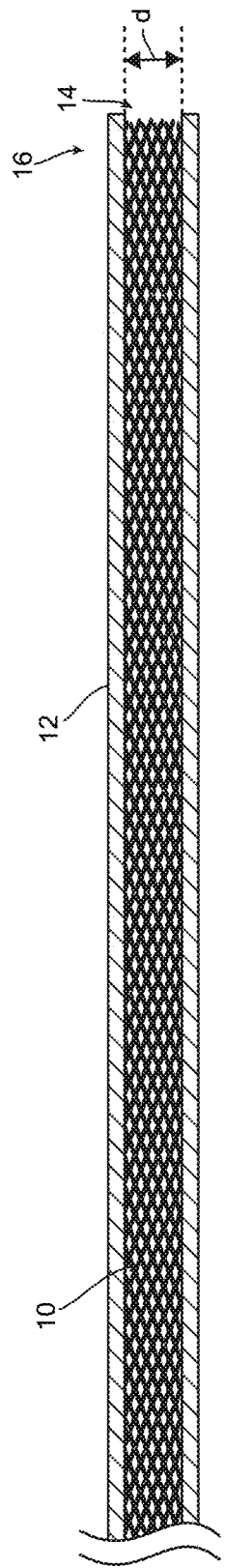
FIG. 1B shows the expandable device of FIG. 1A in a compressed state within a delivery catheter.

The expandable device 10 can be configured to be intravascularly delivered in a compressed state to the treatment site through a delivery catheter. For example, FIG. 1B shows a distal portion of the expandable device 10 in a compressed state positioned within the lumen of a catheter or microcatheter 12 having a distal opening 14. In some embodiments, the expandable device 10 may have an outer diameter or compressed state diameter d in the compressed state of 0.027 inches (0.6858 mm) or less, 0.021 inches (0.5334 mm) or less, 0.017 inches (0.4318 mm) or less, and other suitable diameters. Likewise, the expandable device 10 may be configured to be delivered through a delivery catheter 12 having an inner diameter of 0.027 inches (0.6858 mm) or less, 0.021 inches (0.5334 mm) or less, 0.017 inches (0.4318 mm) or less, and other suitable diameters.

Figure 2A:
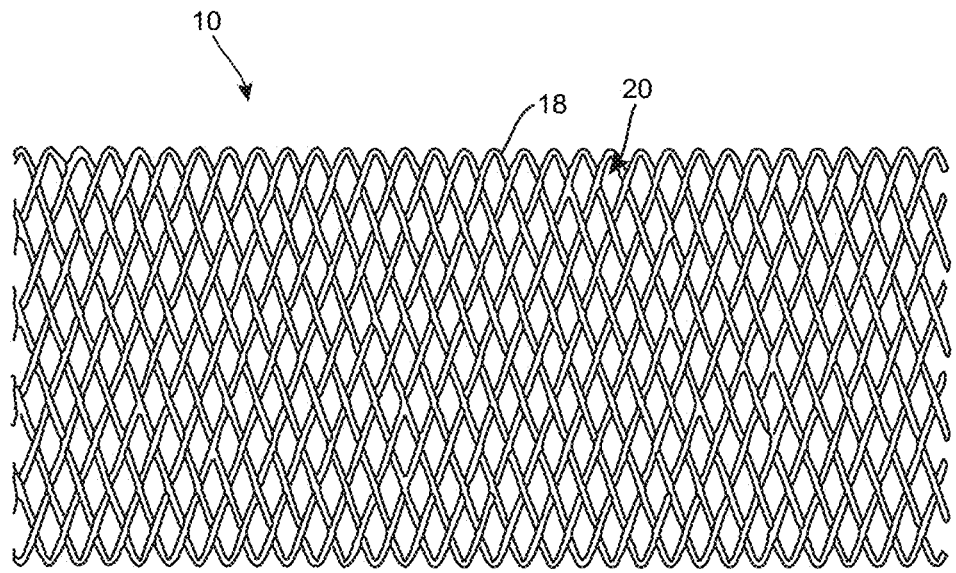
FIG. 2A is an enlarged view of a portion of the expanding device of FIGS. 1A and 1B.
Figure 2B:
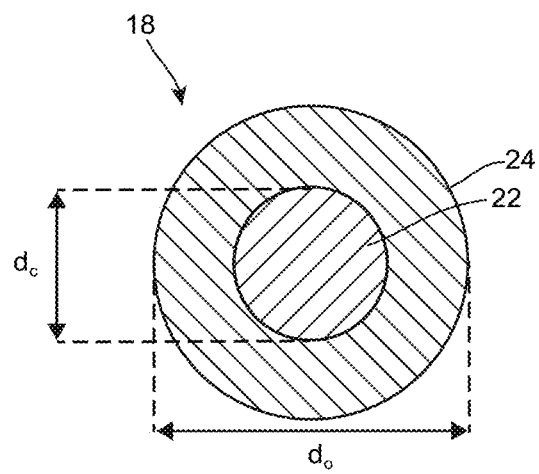
FIG. 2B is an enlarged, cross-sectional end view of a strand of the expandable device of FIGS. 1A and 1B.

FIG. 2A is an enlarged view of a portion of the expandable device 10 in the expanded state, and FIG. 2B is a cross-sectional end view representative of one, some or all of the plurality of strands 18 of some embodiments of the expandable device 10. Referring to FIGS. 2A and 2B, some or all of the strands 18 of the expandable device 10 may have an outer cross-sectional dimension do that is 0.002 inches (50.8 µm) or less. For example, in some embodiments, half (or fewer) of the strands 18 of the expandable device 10 may have an outer cross-sectional dimension do that is 0.002 inches (50.8 µm) or less (or 0.0015 inches (38.1 µm) or less), and each of the remaining strands may have an outer cross-sectional dimension do that is 0.0009 inches (22.86 µm) or less. In some embodiments, the outer cross-sectional dimension do of each of the strands 18 is 0.001 inches (25.4 µm) or less, and in some embodiments, the outer cross-sectional dimension do of each of the strands is 0.0009 inches (22.86 µm) or less, 0.0008 inches (20.32 µm) or less, or 0.0007 inches (17.78 µm) or less. In some embodiments, some or all of the strands 18 may have a circular cross-sectional shape (for example, as shown in FIG. 2B), and the relevant cross-sectional dimension is the diameter of the strands. In some embodiments, some or all of the strands may have other cross-sectional shapes, such as polygonal (e.g., rectangular, square, triangular, etc.), oval-shaped, ellipsoid, and other suitable shapes. In those non-circular embodiments, the relevant cross-sectional dimension is that which comprises the greatest cross-sectional dimension measured orthogonal to the long axis of the strand. In some embodiments, the expandable device 10 may include a mixture of strands 18 having different cross-sectional shapes and/or sizes. In several embodiments, the greater the diameter of the expandable device in the expanded state, the greater the average cross-sectional dimension of the strands.

The expandable devices of the present technology can be at least partially formed of small strands (e.g., strands having a cross-sectional dimension less than 0.001 inches or 25.4 µm), which provide several advantages. For example, the use of small strands decreases the overall profile of the expandable device, thereby allowing the expandable device to be compressed to smaller diameters and delivered to more remote, smaller blood vessels and/or through smaller catheters. The smaller profile in turn reduces in-catheter friction and thus improves the pushability of the expandable device and/or ease of delivery of the expandable device. Including at least some small strands also allows the use of more total strands for larger devices (e.g., having an expanded state diameter or 4 mm or more), which helps maintain a relatively consistent pore size across a range of devices that very widely in implanted or expanded state diameter. Upon implantation, an expandable device with small strands is more easily endothelialized (overgrown and covered with vessel wall tissue), leading to faster healing and elimination of adverse effects (e.g. thrombosis) arising from exposure of blood flow to the material of the strands 18.

The expandable device 10 may include 1, 2, 8, 10, 12, 14, 22, 28, 30, 32, 36, 40, 44, 48, 52, 58, 64, 70, 86, 90, 110, 116, 120, 128, 136, 150, or greater strands that may be assembled or configured to form a tubular braid or weave.

The expandable device 10 and/or strands 18 can be formed from one or more metals, polymers, composites, and/or biologic materials. In some embodiments, the expandable device 10 and/or some or all of the strands 18 thereof may be formed from metal(s) or alloy(s) including superelastic metals/alloys (e.g., nickel-titanium alloys such as Nitinol, etc.) or other metals/alloys such as stainless steel, cobalt-chromium alloys, cobalt-nickel alloys (e.g., 35N LT™ available from Fort Wayne Metals of Fort Wayne, Ind. USA), etc., and be configured to self-expand when released from the delivery catheter 12. In some embodiments, the expandable device 10 and/or some or all of the strands 18 thereof can be formed from platinum, platinum-tungsten alloy, gold, magnesium, iridium, chromium, zinc, titanium, tantalum, and/or alloys of any of the foregoing metals or including any combination of the foregoing metals. In several embodiments, the expandable device 10 and/or some or all of the strands 18 thereof may be highly polished and/or surface treated to further improve hemocompatibility. The expandable device 10 and/or some or all of the strands 18 thereof may be constructed solely from metallic materials without the inclusion of any polymer materials, or may include a combination of polymer and metallic materials. Some or all of the strands 18 may be formed at least in part from radiopaque material, metal or alloy.

In some embodiments, some or all of the strands 18 may be of a bi-component (or multi-component) configuration, for example a coaxial bi-component configuration as shown in FIG. 2B. The coaxial bi-component strand 18 of FIG. 2B comprises an inner core material 22 surrounded by an outer shell material 24. The core material 22 may include any of the materials disclosed in the preceding paragraph, and the outer material 24 may include any of the materials disclosed in the preceding paragraph. In some embodiments, the core material 22 may be different than the outer material 24. For example, in some embodiments, the core material is a radiopaque material (e.g., platinum, platinum-tungsten alloy, tantalum, gold, tungsten, etc., or generally one that is more radiopaque than the outer material 24), and the outer material 24 is a resilient or highly elastic and/or superelastic material (e.g., Nitinol, 35N LT, etc., or generally one that is of higher Young's modulus than the outer material 24). The core material 22 may have a cross-sectional area (based on a cross-sectional dimension dc) that comprises about 5% to about 50%, about 10% to about 45%, about 15% to about 40%, about 10%, about 15%, about 20%, about 25%, about 30%, about 35%, about 40%, about 45% of the total-cross-sectional area of the individual strands (this measure is referred to as the "percent fill" of the strand 18 accounted for by the core material 22).

Some suitable materials and combinations for the strands 18 of the expandable device 10 include: (a) all strands of coaxial bi-component configuration, with a cobalt-nickel outer material and a platinum or platinum-tungsten (or other radiopaque) core material; (b) all strands of coaxial bi-component configuration, with a nickel-titanium outer material and a platinum or platinum-tungsten (or other radiopaque) core material; (c) a combination of some coaxial bi-component strands of cobalt-nickel outer material and a platinum or platinum-tungsten (or other radiopaque) core material, and some single-component strands of cobalt-nickel; (d) a combination of some coaxial bi-component strands of nickel-titanium outer material and a platinum or platinum-tungsten (or other radiopaque) core material, and some single-component strands of nickel-titanium; (e) a combination of some single-component strands of cobalt-nickel or nickel-titanium with some single-component strands of platinum or platinum-tungsten (or other radiopaque material).

As best shown in the enlarged view of FIG. 2A, the strands 18 of the expandable device 10 cross one another to form pores 20. All or a portion of the sidewall of the expandable device 10 may have a flow-diverting porosity when in the expanded state. A "flow diverting porosity" can refer to a porosity that is configured to inhibit the flow of blood through the sidewall into an aneurysm A (FIG. 1A) to a degree sufficient to lead to thrombosis and healing of the aneurysm. (In general, a porosity of the expandable device 10 can be computed as the percentage of the surface area of the sidewall of the expandable device 10 that is accounted for by the pores 20. Porosity can be computed from measured or nominal braid parameters pertaining to a given device.) For example, in some embodiments, the porosity of all or a portion of the expandable device 10 can be from 5% to 95% when in the expanded state. In some embodiments, the porosity of all or a portion of the expandable device 10 may be from 30% to 90%, and in some embodiments, the porosity may be from 50% to 85%, or from 60% to 75%, when in the expanded state. In any of the foregoing examples, although the expandable device 10 may have a porosity configured to reduce hemodynamic flow into and/or induce thrombosis within an aneurysm, the porosity of the expandable device 10 may simultaneously allow perfusion to an adjacent branch vessel (such as branch vessel P in FIG. 1A) whose ostium is crossed by a portion of the expandable device 10.

Instead of or in addition to a flow-diverting porosity as described herein, some or all of the pores 20 of the expandable device 10 may have a flow diverting pore size when the expandable device 10 is in the expanded state. Generally, pore sizes described herein can be measured or computed via the maximum inscribed circle technique, and/or can be an average pore size, and/or a pore size that is computed from measured or nominal braid parameters pertaining to a given device. A "flow diverting pore size" can refer to a pore size (or average pore size) that is sufficiently small to inhibit the flow of blood through the sidewall into an aneurysm to a degree sufficient to lead to thrombosis and healing of the aneurysm when the expandable device 10 is positioned in a blood vessel and adjacent to or across the neck of the aneurysm. For example, a flow diverting pore size can be achieved at a pore size of less than 500 microns when the expandable device 10 is in the expanded state. In some embodiments, a flow-diverting pore size can be between 5 and 450 microns. In some embodiments, a flow-diverting pore size can be less than 320 microns, in the range of 20-300 microns, in the range of 25-250 microns, or in the range of 50-200 microns.

In some embodiments, the expandable device may have an expanded state diameter of 2.5-3.5 mm and include 48 strands, each having a strand outer diameter of 0.0009-0.0013 inches. In such embodiments (or in any other embodiment of the expandable device disclosed herein), the expandable device may optionally have: (a) a radial braid angle in the expanded state of 53-61 degrees, where the radial braid angle is that subtended at the upper or lower vertex of a cell as the expandable device in question is viewed with its lumen extending horizontally (e.g., as in FIG. 2A), (b) an on-mandrel braided picks-per-inch (PPI) of 250-275, and/or (c) a braid pattern of 1-over-2-under-2. In such embodiments, all of the strands may optionally be drawn-filled-tube (DFT) wires with a cobalt-nickel alloy (35NLT) outer annular shell surrounding a concentrically disposed inner cylindrical core of platinum. The DFT wires may be 28%-41% (where the percentage represents the proportion of the total strand cross-sectional area taken up by the core).

In some embodiments, the expandable device may have an expanded state diameter of 4.0-6.0 mm and include 64 strands, each having a strand outer diameter of 0.0009-0.0015 inches. In such embodiments (or in any other embodiment of the expandable device disclosed herein), the expandable device may optionally have: (a) a radial braid angle in the expanded state of 48-55 degrees, where the radial braid angle is that subtended at the upper or lower vertex of a cell as the expandable device in question is viewed with its lumen extending horizontally (e.g., as in FIG. 2A), (b) an on-mandrel braided picks-per-inch (PPI) of 150-200, and/or (c) a braid pattern of 1-over-2-under-2. In such embodiments, all of the strands may optionally be DFT wires with a cobalt-nickel alloy (35NLT) outer annular shell surrounding a concentrically disposed inner cylindrical core of platinum. The DFT wires may be 28%-41% (where the percentage represents the proportion of the total strand cross-sectional area taken up by the core).

In some embodiments, the expandable device 10 may include a coating or surface treatment disposed on at least a portion thereof, for example, on an outer surface of some or all of the strands 18, and/or along some or all of the length of the expandable device 10. Such a coating or surface treatment may be anti-thrombogenic, so as to reduce or minimize the clotting of blood in response to the implantation of the expandable device 10. As employed herein, "anti-thrombogenic" can mean less thrombogenic than the material forming the outer surface of the strands 18 when uncoated or untreated. In some embodiments, the anti-thrombogenic coating or surface treatment comprises a phosphorylcholine, for example 2-methacryloyloxyethyl phosphorylcholine (MPC, available as LIPIDURE™ from NOF Corporation of Tokyo, Japan). A suitable form of MPC is LIPIDURE™-CM2056, or 2-methacryloyloxyethyl phosphorylcholine-poly(n-butyl methacrylate). Other suitable anti-thrombogenic coatings or surface treatments include platelet aggregation inhibitors, and anti-thrombogenic polymers or monomers. These can include PARYLENE C™, or PARYLENE HT™, both available from Specialty Coating Systems of Indianapolis, Ind.; BAYIMEDIX™ available from Bayer AG of Leverkusen, Germany; BIOCOAT™ hyaluronic acid available from BioCoat, Inc. of Horsham, Pa.; or polyethylene oxide. Other suitable anti-thrombogenic materials include heparin, heparin-like materials or derivatives, hirudin, H-Heparin, HSI-Heparin, albumin, phospholipids, streptokinase, tissue plasminogen activator (TPA), urokinase, hyaluronic acid, chitosan, methyl cellulose, poly (ethylene oxide), poly(vinyl pyrrolidone), endothelial cell growth factor, epithelial growth factor, osteoblast growth factor, fibroblast growth factor, platelet derived growth factor or angiogenic growth factor.

Gaining consistent circumferential apposition with the vessel wall is a challenge for many conventional implantable devices. Controlled deployment and precise positioning are even more difficult when using braided or woven devices that foreshorten as they expand. For many conventional devices, the expansion force and shape retention properties of the expandable device are often not sufficient to ensure consistent self-expansion performance. Such challenges are exacerbated in larger diameter devices that must expand to a larger vessel diameter. A device that fails to self-expand adequately can require further intervention from the physician (and risk to the patient) to fully open the expandable device using, e.g. a separate catheter-mounted balloon inserted after initial implantation of the expandable device To address the foregoing shortcomings and challenges of conventional device deployment, certain embodiments of expandable devices disclosed herein are more flexible, compressible to smaller diameters, and deliverable through smaller catheters to more distal locations by inclusion of smaller diameter strands (e.g., less than 0.001 inches or 25.4 µm). Despite use of such smaller diameter strands in some embodiments (and, in other embodiments, the use of strands that are no larger than in conventional devices, e.g. less than 0.002 inches (50.8 µm) or 0.0015 inches (38.1 µm)) devices 10 disclosed herein have improved opening performance and shape retention resulting in part from a high-temperature heat setting process (described in greater detail below with reference to FIGS. 5A and 5B). The expandable devices disclosed herein have improved flexibility, opening force, and shape retention, regardless of the expanded state diameter (e.g., from 1.75 mm to 7 mm), the compressed state diameter, and number of strands. Conventionally, increased flexibility and/or the use of smaller diameter strands are accompanied by a decrease in opening force and shape retention. However, the present technology achieves improvement in both performance measures despite the use of smaller diameter strands (or strands that are no larger than in conventional devices), as discussed in more detail below with reference to FIGS. 5A and 5B.

Figure 3:
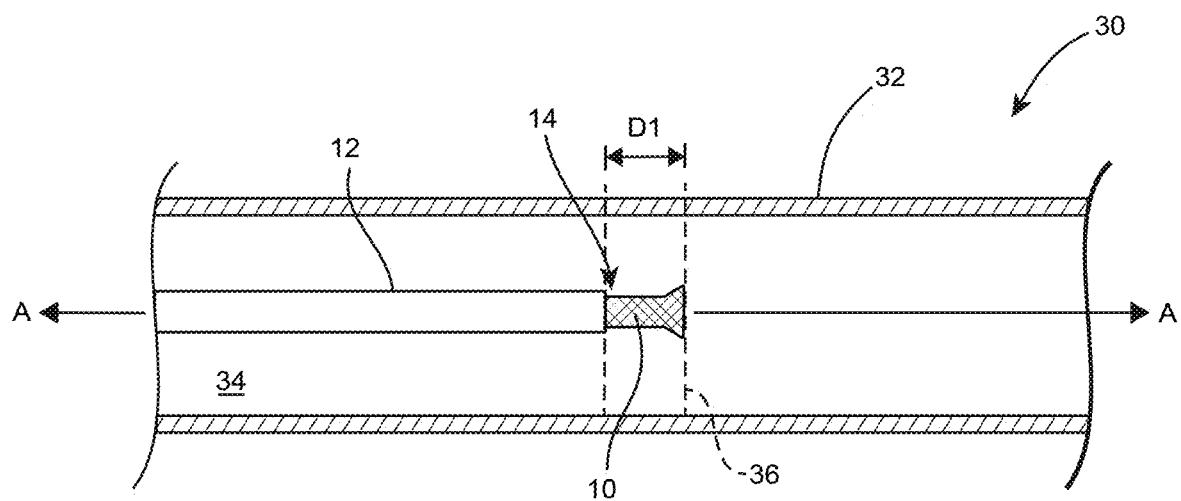
FIG. 3 is a side view of a test fixture and test for a first expansion distance of the expandable device of FIGS. 1A-2B.
Figure 4:
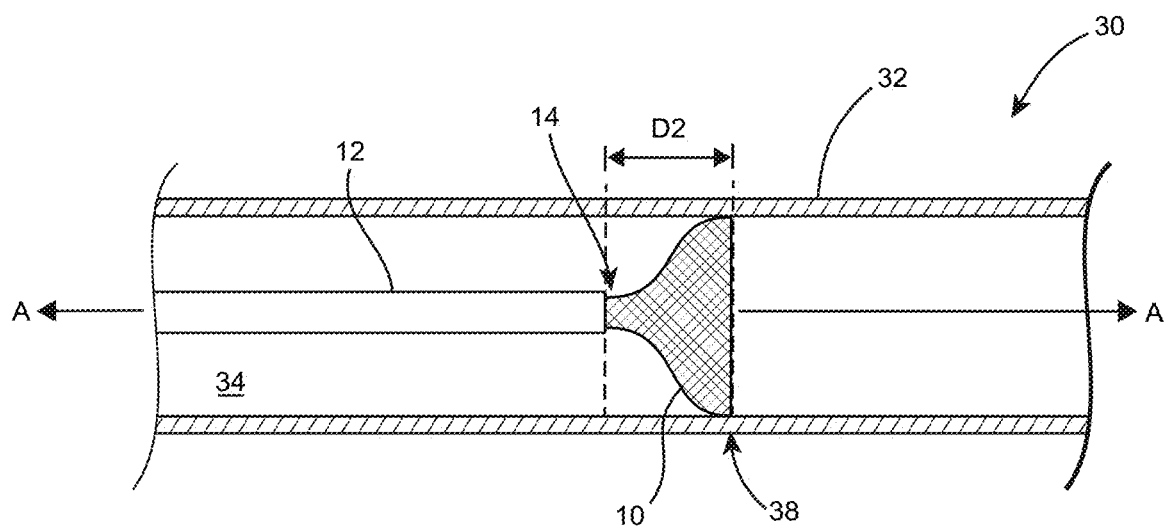
FIG. 4 is a side view of a test fixture and test for a full expansion distance of the expandable device of FIGS. 1A-2B.

FIGS. 3 and 4 depict measures of the longitudinal opening performance of the expandable device 10. A longitudinal test fixture 30 comprises a straight transparent tube 32 having a constant inside diameter corresponding to the expanded state diameter of the expandable device 10 being tested, and a catheter 12 is positioned coaxially in the lumen 34 of the transparent tube 32 along the longitudinal axis A-A thereof. The catheter 12 has an inside diameter of 0.021 inches (for devices having an expanded state diameter of 3.5 mm or less) or 0.027 inches (for devices having an expanded state diameter over 3.5 mm).

To initiate a test, a distal portion of the expandable device 10 is advanced distally from the distal opening 14 of the catheter 12. First, as shown in FIG. 3, the expandable device 10 is advanced to a first expansion point 36 beyond the distal opening 14 of the catheter 12, at which point the distal portion of the expandable device 10 first visibly expands. (This first visible expansion can take place at any point along the portion of the expandable device 10 that has been advanced from the catheter 12, not only at the distal tip as depicted. The first expansion point 36 is therefore the distance by which the distal tip of the expandable device 10 has been advanced from the distal opening 14 of the catheter 12 at the moment when any portion of the advanced device 10 first visibly expands.) The longitudinal distance D1 between the first expansion point 36 and the distal end of the catheter is the "first expansion distance" of the expandable device 10.

As shown in FIG. 4, the expandable device 10 is further advanced to a full expansion point 38 at which the distal end of the expandable device 10 first achieves circumferential apposition with the inner wall of the tube 32. The longitudinal distance D2 between the full expansion point 38 and the distal opening 14 of the catheter 12 is the "full expansion distance" of the expandable device 10.

In some embodiments, the expandable device 10 can achieve a first expansion distance of 12 mm or less, or 10 mm or less, or 9 mm or less, or 8 mm or less, or 7 mm or less, or from 3 mm to 7 mm, over a range of expanded state diameters up to 10 mm, or up to 8 mm, or up to 6 mm, or from 1.75 mm to 10 mm, or from 2 mm to 6 mm, or from 2.5 mm to 6 mm, or greater than or equal to 1.75 mm, 2 mm or 2.5 mm. Devices of expanded state diameter of 3.5 mm or less can do so from a compressed state diameter of 0.021 inches (or 0.021 inches or less), and devices of expanded state diameter of 4.0 mm or more can do so from a compressed state diameter of 0.027 inches (or 0.027 inches or less). Devices of expanded state diameter from 2.5 mm to 3.5 mm can achieve a first expansion distance of 4 mm or less, and devices of expanded state diameter from 4 mm to 6 mm can achieve a first expansion distance of 7 mm or less.

Instead of or in addition to the first expansion distance described herein, in some embodiments, the expandable device 10 can achieve a full expansion distance of 20 mm or less, or 17 mm or less, or 16 mm or less, or 15 mm or less, or 14 mm or less, or from 5 mm to 14 mm, over a range of expanded state diameters up to 10 mm, or up to 8 mm, or up to 6 mm, or from 1.75 mm to 10 mm, or from 2 mm to 6 mm, or from 2.5 mm to 6 mm, or greater than or equal to 1.75 mm, 2 mm or 2.5 mm. Devices of expanded state diameter of 3.5 mm or less can do so from a compressed state diameter of 0.021 inches (or 0.021 inches or less), and devices of expanded state diameter of 4.0 mm or more can do so from a compressed state diameter of 0.027 inches (or 0.027 inches or less). Devices of expanded state diameter from 2.5 mm to 3.5 mm can achieve a full expansion distance of 7 mm or less, and devices of expanded state diameter from 4 mm to 6 mm can achieve a full expansion distance of 14 mm or less.

Selected Methods of Manufacture

The expandable devices 10 of the present technology may be formed by braiding or weaving one or more strands around a mandrel, fixture, or mold (such as a tubular mandrel), and/or by positioning an already-braided or woven structure (such as a tubular braid or weave) onto a mandrel. The mandrel may then be used to hold the braided/woven tubular structure in its desired shape or configuration (typically straight and at constant diameter) while subjected to a heat treatment such that the strands of the braided/woven tubular structure or device 10 assume or are otherwise shape-set to the outer diameter or contour of the mandrel. This can be done to "set" the expandable device 10 at its expanded state diameter such that the expandable device 10, once compressed, will self-expand and return to the expanded state diameter or to the maximum diameter.

Figure 5A:
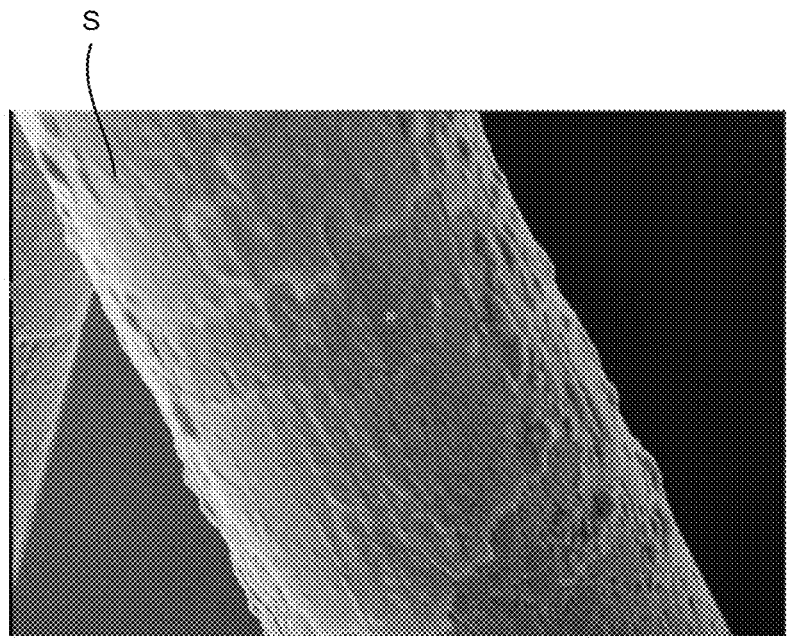
FIG. 5A is a scanning electron microscope (SEM) image showing an outer surface of a strand of an expandable device heat treated according to conventional heat setting processes.

Conventional devices are limited by the heat-treating process in that smaller diameter strands, while generally preferred, require more intense heat treatment parameters (i.e., greater temperatures and/or longer heating times) than larger diameter strands to achieve a desired shape retention profile or opening force. The stronger the heat treatment parameters, however, the greater the thickness of the resulting oxide layer at the outer surface of the strands. FIG. 5A, for example, is an SEM image showing the surface of a strand S heat treated according to conventional heat treatment processes and having a relatively thick oxide layer (i.e., greater than 400 angstroms). Increased oxide layer thickness is generally undesirable as it increases the friction between the strands and the inner surface of the delivery catheter, and also because thicker oxide layers are brittle and may crack when the strands are bent or move across each other at their crossings, thereby creating embolic material. Increased friction between the strands degrades expansion performance, as the strands must slide across each other at their crossings during expansion. To avoid these shortcomings, conventional devices generally either limit or avoid the use of smaller strands, or use smaller strands but sacrifice certain mechanical properties (such as shape retention and expansion performance).

Figure 5B:
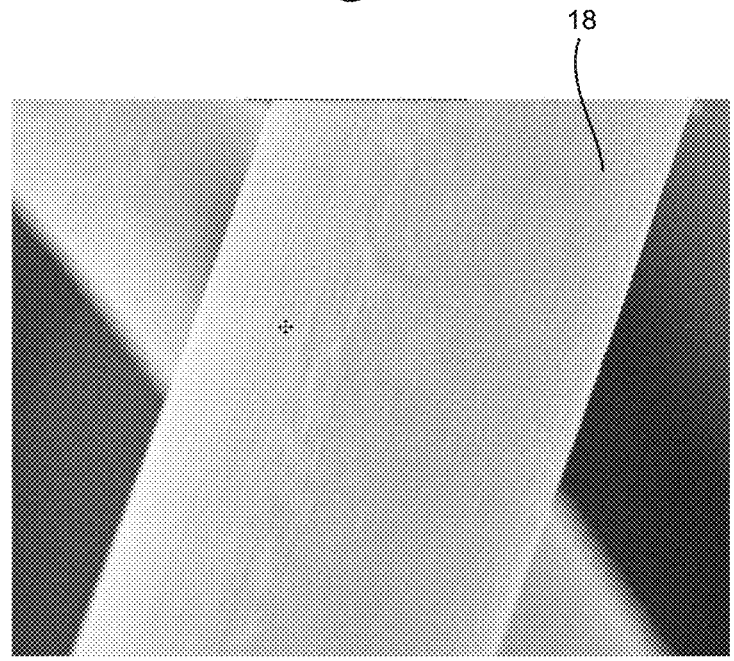
FIG. 5B is an SEM image showing an outer surface of a strand of an expandable device heat treated in according with the present technology.

The present technology includes embodiments of a heat treatment process in which the resulting, heat-treated strands have a significantly reduced oxide layer and improved shape retention, regardless of the size of the strands. FIG. 5B, for example, shows the outer surface of a metallic strand 18 that has been heat treated in accordance with the present technology. As shown in FIG. 5B, the strand 18 has a significantly reduced oxide layer as compared to the strand S heat treated under conventional heat treatment processes, shown in FIG. 5A.

In some embodiments of the present technology, the braided/woven structure or device 10 may be heat treated in an environment substantially or completely depleted of oxygen. For example, the mandrel holding the braided/woven structure or device 10 may be positioned in a gas chamber, and the gas chamber may be purged of oxygen through one or more vacuum stages and/or one or more gas purges. The gas purge, for example, may be a hydrogen gas purge such that, following the vacuum and purging stages, the chamber contains only hydrogen molecules (and does not contain any (or relatively few) oxygen molecules). It is believed that hydrogen gas has a chemically reducing effect with respect to the metallic strands of the expandable device 10 during the heating process. Therefore, any gas having such a chemically reducing effect on the strands may be used in place of hydrogen. The chamber may then be set to a predetermined pressure and temperature for a predetermined length of time.

For example, the braided/woven structure or device 10 (on the mandrel) may be heated in a chamber having a pressure of 5-15 PSI, at a temperature of 600° C. or greater, 610° C. or greater, 615° C. or greater, 620° C. or greater, 625° C. or greater, 630° C. or greater, 635° C. or greater, 640° C. or greater, 645° C. or greater, 650° C. or greater, 655° C. or greater, 660° C. or greater, 665° C. or greater, 670° C. or greater, 675° C. or greater, 680° C. or greater, 685° C. or greater, 690° C. or greater, 695° C. or greater, 700° C. or greater, 705° C. or greater, 710° C. or greater, 715° C. or greater, 720° C. or greater, 725° C. or greater, about 600° C. to about 700° C., about 625° C. to about 700° C., about 650° C. to about 750° C., about 675° C. to about 750° C., or about 675° C. to about 700° C., for a time at least 1 minute, at least 2 minutes, at least 3 minutes, at least 4 minutes, at least 5 minutes, at least 7 minutes, at least 10 minutes, at least 12 minutes, at least 13 minutes, at least 15 minutes, at least 18 minutes, at least 20 minutes, at least 22 minutes, at least 25 minutes, at least 27 minutes, at least 30 minutes, and other suitable time periods.

After the braided/woven structure or device 10 has been heat set as detailed above, each of the strands may have an oxide layer thickness of less than 400 angstroms. In some embodiments, after the structure or device 10 has been heat set, each of the strands 18 may have an oxide layer thickness of about 10 angstroms to about 400 angstroms, about 100 angstroms to about 350 angstroms, about 200 angstroms to about 350 angstroms, or about 200 angstroms to about 300 angstroms. The relatively thin oxide layer provides the corresponding strand with a smoother outer surface (as demonstrated by comparison of FIGS. 5A and 5B), thus decreasing the overall friction between the strands of the expandable device 10, and between the expandable device 10 and the inner surface of the delivery catheter 12. Therefore, at least one advantage of the heat setting processes of the present technology is providing an expandable device with improved ease of delivery. In addition, the reduced friction promotes better device opening/expansion performance, as the strands 18 must slide across each other at their crossings when the expandable device 10 expands. This in turn allows for good opening or expansion performance even with small-diameter wires.

In addition to a reduced oxide layer thickness, the heat setting methods of the present technology provide expandable devices with improved shape retention properties. For example, when the expandable device is removed from the mandrel and allowed to expand, the expandable device has a braid picks-per-inch measurement (PPI) that is at least 90% of its PPI when on the mandrel. In some embodiments, the expandable device may have a PPI that is at least 92%, at least 94%, at least 96%, at least 98%, or at least 99% of its on-mandrel PPI.

A number of devices 10 were prepared according to Table 1:

TABLE 1

| Expanded State Diameter (mm) | Strand Count | Strand Outside Diameter (inches) | Strand Configuration* | Radial Braid Angle** - Expanded State (degrees) | Braided PPI (on mandrel) | Braid Pattern |
|---|---|---|---|---|---|---|
| 2.5-3.5 | 48 | .0009-.0013 | 28%-41% fill DFT | 53-61 | 250-275 | 1-over-2-under-2 |
| 4.0-6.0 | 64 | .0009-.0015 | 28%-41% fill DFT | 48-55 | 150-200 | 1-over-2-under-2 |

*All strands are drawn-filled-tube (DFT) wires with a cobalt-nickel alloy (35NLT) outer annular shell surrounding a concentrically disposed inner cylindrical core of platinum. "Percent fill" refers to the proportion of the total strand cross-sectional area taken up by the core. The balance of the cross-sectional area is taken up by the outer shell.
**The radial braid angle is that subtended at the upper or lower vertex of a cell as the expandable device in question is viewed with its lumen extending horizontally (e.g., as in FIG. 2A).

Some devices 10 were constructed by braiding according to Table 1 and heat treated as follows. The expandable devices were placed on mandrels having a diameter corresponding to the expanded state diameters of the expandable devices (less the expandable devices' wall thicknesses) in a pressure chamber which was evacuated and then filled with hydrogen gas at 5 PSI. The pressure chamber, with devices inside, was then placed in an oven, and heated at 675° C. for 15 minutes. The chamber and devices were then removed and allowed to cool to room temperature. The pressure chamber was equipped with an inlet and outlet valve arrangement to regulate the hydrogen gas pressure within the range of 5-15 PSI throughout the heat treatment.

Devices 10 made in this manner can achieve expansion performance as follows. (See FIGS. 3-4 regarding the test equipment and technique.) Devices in the 2.5-3.5 mm range of expanded state diameter can achieve a first expansion distance of 3.12-3.26 mm, and a full expansion distance of 5.16-5.88 mm. Devices in the 4.0-6.0 mm range of expanded state diameter can achieve a first expansion distance of 3.99-6.46 mm, and a full expansion distance of 8.97-13.58 mm.

The expandable devices disclosed herein may include any combination of any of the parameters and/or performance measures (distinct values and/or ranges thereof) disclosed herein, such as any of the compressed state diameters disclosed in the present Detailed Description (for example, as discussed with reference to FIGS. 1A-1B), any of the expanded state diameters disclosed in the present Detailed Description (for example, as discussed with reference to FIGS. 1A-1B), any of the strand cross-sectional dimensions and shapes disclosed in the present Detailed Description (for example, as discussed with reference to FIGS. 1C-1D), any of the strand materials disclosed in the present Detailed Description, any of the PPI values or ranges disclosed in the present Detailed Description, any of the longitudinal opening performance metrics disclosed in the present Detailed Description (for example, as discussed with reference to FIGS. 3-4), any of the shape retention properties disclosed in the present Detailed Description (for example, as discussed with reference to FIGS. 5A-5B), any of the oxide layer thicknesses disclosed in the present Detailed Description (for example, as discussed with reference to FIGS. 5A-5B), any of the porosities disclosed in the present Detailed Description, any of the coverages disclosed in the present Detailed Description, etc. All possible combinations of the foregoing parameters and/or performance measures are included in the present technology. As but one of many examples, the expandable device 10 may be formed of 48 strands, each having an oxide layer thickness of about 400 angstroms or less, where each of half of the strands has a diameter of 0.002 inches (50.8 µm) or less and each of half of the strands has a diameter of less than 0.001 inches (25.4 µm). The strands may have an inner radiopaque material surrounded by an outer resilient material. The foregoing device 10 may be compressible to a diameter of 0.021 inches (0.5334 mm) or less, have a diameter in the expanded state that is about 2.75 mm to about 3.75 mm, and have a PPI of 250 to 275. As another of many examples, in some embodiments the expandable device 10 may be formed of 64 strands, each having an oxide layer thickness of about 400 angstroms or less, and where each of at least some of the strands has a diameter of 0.001 inches (25.4 µm) to about 0.002 inches (50.8 µm) and each of at least some of the strands has a diameter of less than 0.001 inches (25.4 µm). The strands may have an inner radiopaque material surrounded by an outer resilient material. The foregoing device 10 may be compressible to a diameter of 0.021 inches (0.5334 mm) or less, have a diameter in the expanded state that is about 4.25 mm to about 6.25 mm, and have a PPI of 150 to 200.

Selected Methods of Use

As mentioned elsewhere herein, the present disclosure includes methods of treating a vascular condition, such as an aneurysm, with any of the embodiments of the expandable devices disclosed herein. The expandable device could be deployed across the neck of an aneurysm and its flow-diverting properties employed to impede blood flow between the aneurysm and the parent vessel, cause the blood inside the aneurysm to thrombose, and lead to healing of the aneurysm. The expandable devices disclosed herein may also be used to treat other vascular defects. For example, the expandable devices of the present technology may be used to remove clot material from a blood vessel (e.g., as a thrombectomy device), or in angioplasty by deploying the stent across a plaque or lesion to improve or maintain vessel patency, or in other vascular stenting procedures.

In order to implant any of the expandable devices disclosed herein, the expandable device can be mounted in a delivery system, such as any of the delivery systems disclosed in U.S. application Ser. No. 15/410,444, filed Jan. 19, 2017, titled COUPLING UNITS FOR MEDICAL DEVICE DELIVERY SYSTEMS, which is incorporated by reference herein in its entirety. For example, an end region of the expandable device can be configured to be detachably coupled to an elongate delivery system. Generally, the delivery system can comprise an elongate core member that engages, supports or contains the expandable device, and both components can be slidably received in a lumen of a microcatheter (e.g., a 0.017", 0.021", 0.027" microcatheter) or other elongate sheath for delivery to any region to which the distal opening of the microcatheter can be advanced. The core member is employed to advance the expandable device through the microcatheter and out the distal end of the microcatheter so that the expandable device is allowed to self-expand into place in the blood vessel, across an aneurysm (e.g., as in FIG. 1A), across a plaque or lesion, against a blood vessel or body lumen wall, or other treatment location. Accordingly, a vascular treatment apparatus can comprise a delivery system, such as any of the delivery systems described herein, and an expandable device, such as any of the expandable devices described herein, mounted in or on the delivery system.

A treatment procedure can begin with obtaining percutaneous access to the patient's arterial system, typically via a major blood vessel in a leg or arm. A guidewire can be placed through the percutaneous access point and advanced to the treatment location, which can be in a intracranial artery, or any neurovascular artery or vein, or a peripheral, coronary, pulmonary, abdominal, thoracic or aortic artery, or any bodily lumen. The catheter or microcatheter is then advanced over the guidewire to the treatment location and situated so that a distal open end of the catheter or microcatheter is adjacent to the treatment location. The guidewire can then be withdrawn from the microcatheter and the core member, together with the expandable device mounted thereon or supported thereby, can be advanced through the microcatheter and out the distal end thereof. The expandable device can then self-expand into apposition with the inner wall of the blood vessel. Where an aneurysm is being treated, the expandable device is placed across the neck of the aneurysm so that a sidewall of the expandable device separates the interior of the aneurysm from the lumen of the parent artery (e.g., as in FIG. 1A). In an angioplasty procedure, the expandable device is placed across the target plaque or lesion to maintain vessel patency, and in other stenting procedures, the expandable device is placed against the inner wall of the blood vessel or bodily lumen in need of support or therapy.

Once the expandable device has been placed, the core member and microcatheter are removed from the patient. In an aneurysm treatment, all or a portion of the expandable device sidewall can now perform a flow-diverting function on the aneurysm, thrombosing the blood in the aneurysm and leading to healing of the aneurysm.

CONCLUSION

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

It is understood that the specific order or hierarchy of steps in the processes disclosed is an illustration of exemplifying approaches. Based upon design preferences, it is understood that the specific order or hierarchy of steps in the processes may be rearranged. Some of the steps may be performed simultaneously. Various methods are disclosed presenting elements of the various steps in a sample order, and are not meant to be limited to the specific order or hierarchy presented.

Furthermore, to the extent that the term "include," "have," or the like is used herein, such term is intended to be inclusive in a manner similar to the term "comprise" as "comprise" is interpreted when employed as a transitional word in a Clause.

A reference to an element in the singular is not intended to mean "one and only one" unless specifically stated, but rather "one or more." The term "some" refers to one or more. The term "about" includes the stated value and a variation of up to ±5% in the value. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The numbered clauses and their equivalents are intended to cover such forms or modifications as would fall within the scope and spirit of the subject technology.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. The foregoing definition also applies to the use of "and/or." Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An expandable device implantable across an aneurysm in a blood vessel of a patient, the expandable device comprising:
   a generally tubular structure formed of a plurality of braided metallic strands, the tubular structure having a proximal end, a distal end, and a length between the proximal end and the distal end;
   a compressed state in which the expandable device has a compressed state diameter of 0.027 inches or less;
   an expanded state in which the expandable device has an expanded state diameter corresponding to the expandable device, the expanded state diameter being 1.75 mm or more,
   wherein each of the plurality of metallic strands has an oxide layer having a thickness of about 400 angstroms or less, wherein the oxide layer (a) is essentially free of titanium, and (b) includes cobalt and/or chromium, wherein the oxide layer is formed at least in part by a heat treatment and
   wherein the tubular structure is configured to self-expand from the compressed state to the expanded state.

2. The expandable device of claim 1, wherein the oxide layer thickness is between 10 angstroms and 400 angstroms.

3. The expandable device of claim 1, wherein the oxide layer thickness is between 100 angstroms and 350 angstroms.

4. The expandable device of claim 1, wherein the oxide layer thickness is between 200 angstroms and 350 angstroms.

5. The expandable device of claim 1, wherein the oxide layer thickness is between 200 angstroms and 300 angstroms.

6. The expandable device of claim 1 wherein each of the plurality of strands has a diameter that is less than or equal to 0.002 inches (0.0508 mm).

7. The expandable device of claim 1 wherein each of the plurality of strands has a diameter that is less than or equal to 0.0015 inches (0.0381 mm).

8. The expandable device of claim 1 wherein each of the plurality of strands has a diameter that is less than or equal to 0.002 inches (0.0508 mm), and at least some of the plurality of strands have individual diameters less than or equal to 0.0009 inches (0.02286 mm).

9. The expandable device of claim 1, wherein the compressed state diameter is 0.017 inches (0.4318 mm) or less.

10. The expandable device of claim 1, wherein the compressed state diameter is 0.017-0.027 inches.

11. The expandable device of claim 1, wherein the expanded state diameter is 2 mm or more.

12. The expandable device of claim 1, wherein the expanded state diameter is 2-10 mm.

13. The expandable device of claim 1, wherein the expanded state diameter is 2-6 mm.

14. The expandable device of claim 1, wherein the braided strands form a sidewall of the tubular structure with a number of pores between the strands, and the pores are sized to have a flow-diversion effect with respect to an aneurysm when the sidewall extends across the aneurysm.

15. The expandable device of claim 1, wherein the braided strands form a sidewall of the tubular structure with a number of pores between the strands, and the sidewall has a porosity measure that is sufficient to have a flow-diversion effect with respect to an aneurysm when the sidewall extends across the aneurysm.

16. The expandable device of claim 1, wherein the tubular structure defines a lumen, and has openings at the proximal and distal ends of the structure.

17. The expandable device of claim 16, wherein the lumen is non-filtering and open to flow of liquid therethrough.

18. The expandable device of claim 1, wherein the tubular structure consists of the braided strands.

19. The expandable device of claim 1, wherein the braided strands alone are sufficient to cause the tubular structure to self-expand to the expanded state.

20. The expandable device of claim 1, wherein the strands collectively comprise a first metallic material and a second metallic material, and the second metallic material is more radiopaque than the first metallic material.

21. The expandable device of claim 20, wherein the second metallic material comprises platinum or platinum alloy.

22. The expandable device of claim 1, wherein the expanded state diameter is a diameter to which the expandable device will self-expand, and is 2.5%-12.5% below the expandable device's maximum unconstrained self-expansion diameter.

23. The expandable device of claim 1, wherein the tubular structure is heat set to self-expand toward the expanded state diameter.

24. The expandable device of claim 1, wherein the strands possess an anti-thrombogenic outer surface.

25. The expandable device of claim 1, wherein the compressed state diameter is 0.021 inches (0.5334 mm) or less.

26. The expandable device of claim 1, wherein the oxide layer thickness is at least 10 angstroms.

27. An expandable device implantable across an aneurysm in a blood vessel of a patient, the expandable device comprising:
   a generally tubular structure formed of a plurality of braided metallic strands, wherein each of the plurality of strands has a diameter that is less than or equal to 0.002 inches (0.0508 mm); and
   an expanded state in which the expandable device has an expanded state diameter corresponding to the expandable device, the expanded state diameter being 1.75 mm or more;
   wherein each of the plurality of metallic strands has an oxide layer having a thickness of about 400 angstroms or less, wherein the oxide layer (a) is essentially free of titanium and (b) includes cobalt and/or chromium, wherein the oxide layer is formed at least in part by a heat treatment, and
   wherein the tubular structure is configured to self-expand from a compressed state to the expanded state.

28. The expandable device of claim 27, wherein the oxide layer thickness is between 10 angstroms and 400 angstroms.

29. The expandable device of claim 27, wherein the oxide layer thickness is between 100 angstroms and 350 angstroms.

30. The expandable device of claim 27, wherein the oxide layer thickness is between 200 angstroms and 350 angstroms.

31. The expandable device of claim 27, wherein the oxide layer thickness is between 200 angstroms and 300 angstroms.

32. The expandable device of claim 27, wherein the braided strands alone are sufficient to cause the tubular structure to self-expand to the expanded state.

33. The expandable device of claim 27, wherein the oxide layer thickness is at least 10 angstroms.

* * * * *